United States Patent [19]
Ansorge

[11] Patent Number: 5,124,247
[45] Date of Patent: Jun. 23, 1992

[54] PROCESS FOR SEQUENCING NUCLEIC ACIDS

[75] Inventor: Wilhelm Ansorge, Gaiberg/Heidelberg, Fed. Rep. of Germany

[73] Assignee: Europäisches Laboratorium Für Molekularbiologie (Embl), Heidelberg, Fed. Rep. of Germany

[21] Appl. No.: 448,726

[22] Filed: Dec. 11, 1989

[30] Foreign Application Priority Data

Dec. 9, 1988 [DE] Fed. Rep. of Germany ....... 3841565

[51] Int. Cl.$^5$ ..................... C12Q 1/68; C12P 19/34; G01N 33/48; C07H 15/12
[52] U.S. Cl. ........................................ 435/6; 435/91; 436/94; 436/501; 536/26; 536/27; 536/28; 536/29; 935/77; 935/78
[58] Field of Search ............... 435/6, 91; 436/501, 436/94; 935/77, 78; 536/26, 27, 28, 29

[56] References Cited

U.S. PATENT DOCUMENTS 4,683,195 7/1987 Mullis et al. .................... 935/77

OTHER PUBLICATIONS

Ansorge et al., Nuc. Acids Res. 15(11): 4593–4602 (Jun. 11, 1987).
Ansorge et al., Nuc. Acids Res. 18(11): 3419–3420 (1990).
Kristensen et al., Nuc. Acids Res. 16(8): 3487–3496 (1988).

Primary Examiner—Robert A. Wax
Assistant Examiner—Stephanie W. Zitomer
Attorney, Agent, or Firm—Felfe & Lynch

[57] ABSTRACT

For the sequencing of nucleic acids by enzymatic extension of an oligonucleotide primer in the presence of a polymerase, the four deoxyribonucleoside triphosphates, one of the four dideoxynucleoside triphosphates and the nucleic acid to be sequenced as template in each of four different preparations, labelling of the nucleic acid fragments which form and which are dependent on the dideoxynucleoside triphosphate used, separation by gel electrophoresis of the preparations containing the fragments and detection of the sequence via the label, at least two of the dideoxynucleoside triphosphates are used in different amounts together in one preparation and the fragments are differentiated by the intensity of the labelling signal of the bands in the gel or in another separation procedure.

25 Claims, 2 Drawing Sheets

PROCESS FOR SEQUENCING NUCLEIC ACIDS

DESCRIPTION

The invention involves an improvement on a process for sequencing nucleic acids. The process which is improved is one in which an oligonucleotide primer is extended in the presence of (i) a polymerase, (ii) all four deoxyribonucleoside triphosphaes, (iii) a single dideoxynucleoside triphosphate, and (iv), the nucleic acid to be sequenced, which acts as a template. In this known process, four different preparations, each of which uses a different dideoxyribonucleoside are required. Nucleic acid fragments form, which are then labelled. The fragments which form depend upon which of the dideoxyribonucleosides is used. The fragments thus formed are separated via gel electrophoresis, and the fragment is then determined via its incorporated label.

In order to sequence DNA, two methods are generally known. The first is the chemical degradation procedure according to Maxam and Gilbert (A. M. Maxam and W. Gilbert, Proc. Natl. Acad. Sci. USA 74 (1977), 560 and A. M. Maxam and W. Gilbert, Methods in Enzymol. vol. 65, (1980) p. 499). The second is and the enzymatic dideoxy chain termination method (F. Sanger et al., Proc. Natl. Acad. Sci. USA 74 (1977), 5463-5467). Using the method according to Sanger one starts with a DNA template, and produces many labelled DNA molecules of differing length by enzymatic extension of a synthetic primer, using DNA polymerase and a mixture of deoxy- and dideoxynucleoside triphosphates. To do this, a mixture of a certain deoxynucleoside triphosphate and a corresponding dideoxynucleoside triphosphate together with the three other deoxynucleoside triphosphates is used in each of four preparations. Each preparation contains a different dideoxynucleoside. In this way statistical incorporation of the dideoxynucleotides into the growing DNA chain is achieved, because after a dideoxynucleotide is incorporated into a DNA chain, it cannot grow any longer because of the absence of a 3'-OH group. Thus, many DNA fragments are formed which from a statistical point of view, contain at least one dideoxynucleoside at every possible incorporation site and which end there. These four preparations with fragmetns each ending at the positions of one base are each separated in one lane on polyacrylamide gels and the sequence is determined after autoradiography.

In the Maxam-Gilbert method end-labelled DNA molecules are modified chemically in a base-specific manner, partial strand termination is effected and the fragments thus obtained are separated by polyacrylamide gel electrophoresis. The sequence is determined after autoradiography.

Both known methods have advantages and disadvantages. An advantage of the Sanger dideoxy method is that the label and the production of base-specific fragments can be combined in one step, Also, single-stranded as well as double-stranded DNA can be sequenced. Furthermore, the sequencing of longer DNA fragments is made possible by so-called "shot-gun" experiments in M13-descendants etc. Until about 1986, DNA sequencing was carried out using radioactive ($^{32}P$ or $^{35}S$) labels. After gel electrophoresis and autoradiography the nucleotide sequence was determined either manually or semi-automatically. Since then, fluorescence labelling has also been used for dideoxy sequencing (L. M. Smith et al., Nature, 321 (1986) 674-679; W. Ansorge et al., J. Biochem. Biophys. Meth. 13 (1986) 315-323). Using this procedure, the nucleotide sequence can be read automatically during the electrophoresis and can be directly entered into a computer.

In contrast the Maxam-Gilbert method is used reluctantly for sequencing long DNA fragments because of the following disadvantages: the labelling of the DNA and the formation of base-specific fragments have to be carried out in two separate steps and, the available labelling techniques are complicated and require the presence of suitable restriction sites on the nucleic acids to be sequenced. In addition to this, four steps have to be carried out for standard labelling methods according to Maxam and Gilbert, i.e. the cleavage of DNA with a restriciton endonuclease, the enzymatic labelling, cleavage of the labelled DNA fragments with a second restriction endonuclease so that the labelled DNA fragments are only labelled on one end and isolation of the DNA fragments which are only labelled at one end by agarose- orpolyacrylamide gel electrophoresis.

Further disadvantages of the Maxam-Gilbert method include the fact that sequencing of single-stranded DNA is not easy to carry out, and random or systematic strategies, as they are carried out in connection with the enzymatic dideoxy method, cannot be used for sequencing long DNA fragments. In addition, the chemical reactions in solution (as described by Maxam and Gilbert) are laborious because of the precipitation steps needed. The Maxam and Gilbert process has only been described in connection with radioactive labelling.

As a result of the disadvantages of the Maxam-Gilbert method, sequencing of DNA nowadays is usually carried out according to the method of Sanger et al. Both methods present a serious disadvantage in that this method requires the four different extension reactions to be carried out in different preparations and loaded on different lanes of a gel for gel electrophoresis. Because of a this only the fragments of relatively few sequencing preparations can be loaded on a gel carrying out four different preparations for every nucleic acid to be sequenced is exceedingly laborious and time-consuming.

it is therefore the object of the present invention to avoid these disadvantages of the sequencing method according to Sanger et al., and to make available a sequencing method which can be carried out quickly and simply based on the well known method according to Sanger et al.

The object of the present invention is therefore a process for sequencing nucleic acids by enzymatic extension of an oligonucleotide primer in the presence of a polymerase, the four deoxyribonucleoside triphosphates, one of the four dideoxynucleoside triphosphates and the nucleic acid to be sequenced as template in each of four different preparations, labelling of the nucleic acid fragments which form and which are dependent on the dideoxynucleoside triphosphate used, separation of the preparations containing the fragments by gel electrophoresis and detection of the sequence via the label, characterized in that at least two of dideoxynucleoside triphosphates are used in different amounts in one preparation, wherein the fragments are differentiated by the intensity of the labelling signal of the bands in the gel or in another separation procedure.

The process according to the present invention allows sequencing to be carried out in for example only two preparations or only one each of which contains two of the dideoxynucleoside triphosphates and which consequently are loaded on only two lanes of a gel. This is made possibly by the use of the dideoxynucleoside triphosphates in different amounts so that in the separation procedure the bands of the fragments which result from the use of the one dideoxynucleoside triphosphate occur more frequently than bands of fragments with terminations at the positions of the dideoxynucleoside triphosphate present in a smaller amount. Thus in the sequence detection the bands can be assigned to the bases of the sequence by means of the signal intensity of the label.

In a preferred embodiment of the invention two dideoxynucleoside triphosphates are used together in a preparation in a quantity ratio of at least 2:1.

In a particularly preferred embodiment of the invention all four dideoxynucleoside triphosphates are used in one preparation in a ratio of at least 4:3:2:1. By use of this particularly preferred procedure the sequencing of nucleic acids is possible in only one preparation and after loading on only one lane of a sequencing gel. The ratio of 4:3:2:1 is the lowest limit and, in order to increase the accuracy of the sequencing, ratios with a greater difference between the individual dideoxynucleoside triphosphates should be used. These differences in the ratio of the dideoxynucleoside triphosphates also depend on the polymerase enzyme used because enzymes which yield uniform peak patterns can be used with a lower ratio of the deoxynucleoside triphosphates than polymerase which do not yield such uniform peaks.

Even though all labelling methods for the sequencing according to Sanger are suitable for the procedure according to the present invention such as e.g. radioactive labelling, it is preferable to use a fluorescent dye for the label. In a particularly preferred embodiment of the invention a primer coupled to a fluorescent dye is used for the label. The fluorescent dye is preferably bound to the 5'-phosphate group of the primer via a linker (FIG. 1A).

In another particularly preferred embodiment of the invention a deoxy- or dideoxynucleoside triphosphate bound to a fluorescent dye via a linker is used for the label. In this connection it is especially preferred to use a labelled deoxynucleoside triphosphate since the nucleic acid fragment which forms can thus be labelled several times whereas when labelling via dideoxynucleoside triphosphates or via a primer with a fluorescent label at the 5'-phosphate group only one fluorescent dye group is bound to each nucleic acid fragment which forms. The intensity of the signal can therefore be increased using this preferred embodiment of the invention.

When using labelled deoxy- or dideoxynucleoside triphosphates it is preferably to use those in which the dye is coupled via a linker to the C5 position of pyrimidines or to the N7, C8 or C7 position of purines.

Within the scope of the invention straight-chain or branched amino- or mercapto-hydrocarbon units with more than two carbon atoms in the unbranched chain are preferably used as the linker. Especially preferred for this are aminoalkyl, aminoalkenyl or aminoalkynyl groups.

Within the scope of the invention single- or double-stranded nucleic acids can be used as the nucleic acids to be sequenced. According to the present invention fluorescein, analogues thereof or rhodamine are preferably used as markers. Fluorescein is particularly preferred.

In a preferred embodiment, the process according to the present invention is carried out in such a way that two different dideoxynucleoside triphosphates in a ratio of 5:1, 6:1 or 7:1 are used in each of two preparations. In this way, the strongest bands in each of the two lanes of the gel on which both preparations have been loaded can be identified as belonging to the dideoxynucleoside triphosphates that have been used in a larger amount and the other bands belong to the bases whose dideoxynucleoside triphosphate was used in the smaller amount.

In another particularly preferred embodiment of the invention all four different dideoxynucleoside triphosphates are used in only one preparation in a ratio of 16:8:4:1. Using these ratios, differentiation of the dideoxynucleoside triphosphates is possible and therefore the base sequence can be easily read.

According to the present invention it is also possible to carry out the sequencing with only three of the four differential dideoxynucleoside triphosphates. In this connection either all three dideoxynucleoside triphosphates are used in one preparation or else two dideoxynulceoside triphosphates are used in one preparation and only one dideoxynucleoside triphosphate is used in a second preparation. After separation, for example in a polyacrylamide gel, bands with different signal intensities appear in regular intervals whereby a gap occurs in the band pattern at the position of the base in the nucleic acid to be sequenced corresponding to the missing dideoxynucleoside triphosphate.

For the extension of nucleotide sequences according to the present invention the Klenow fragment of the DNA polymerase I, modified or unmodified T7 DNA polymerase, Taq polymerase or reverse transcriptase are preferred. Of these polymerases, unmodified T7 DNA polymerase is especially preferable because it results in a particularly uniform peak pattern.

In a scope of the invention, it may be necessary, or preferred, to increase or to amplify the amount of double stranded nucleic acid to be sequenced and which serves as template. This can be done via use of, e.g., the polymerase chain reaction (PCR) as taught in U.S. Pat. Nos. 4,683,195; 4,683,202 and 4,800,159. In this method, the double stranded nucleic acid to be sequenced is combined with two synthetic primers in the presence of all four deoxynucleosides triphosphates and a polymerase. A cycle takes place, and is repeated many times. The "cycle" involves extending the primer, heating to separate strands, adding new polymerase, separating the extension products of both strands, and then using one strand for sequencing. This methodology allows one to sequence, e.g., DNA, which is present in only small quantities in the sample.

The method of detection according to the present invention corresponds to the type of label used in each case. Radioactively labelled fragments are thus visualized by autoradiography of the gel. In the preferred embodiment the present invention a fluorescent dye is used which is excited preferably by a laser after separation of the fragments by gel electrophoresis and by this means a particularly strong signal is obtained. Using the preferred detection method according to the present invention the detection can also be carried out in an apparatus which detects the bands simultaneously with the gel electrophoresis and immediately transmits them to a computer which automatically prints out the sequence of the nucleic acid to be sequenced.

The process according to the present invention allows many different nucleic acids to be rapidly and easily sequenced side by side and to be simultaneously loaded on a gel. It is also possible, after the run has been completed to reload the single lanes of the gel with a new nucleic acid to be sequenced by use of the preferred fluorescent labelling and the automatic detection. Also by this means the sequencing of many different DNA fragments can be accelerated decisively.

BRIEF DESCRIPTION OF THE FIGURES

FIG. 3 shows parts of the DNA sequence of the bacteriophage M13mp18.

DETAILED DESCRIPTION OF PREFERRED EMBODIMENTS

Figure 1A:
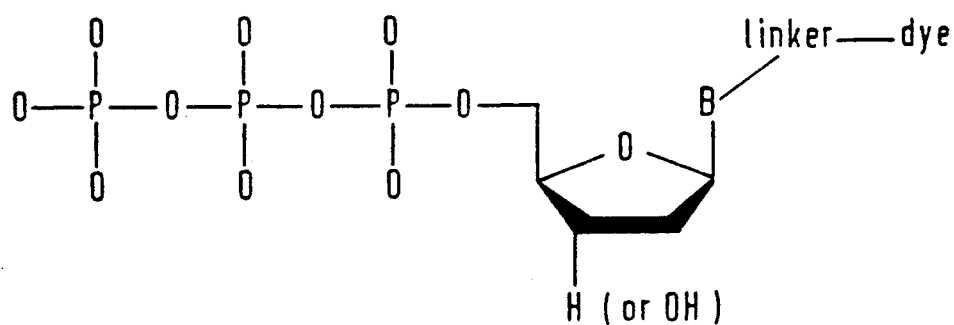
FIGS. 1A and 1B show the position of the fluorescent dye label on a deoxynucleoside triphosphate or dideoxynucleoside triphosphate (FIG. 1A) and on an oligonucleotide primer (FIG. 1B) used according to the present invention.
Figure 1B:
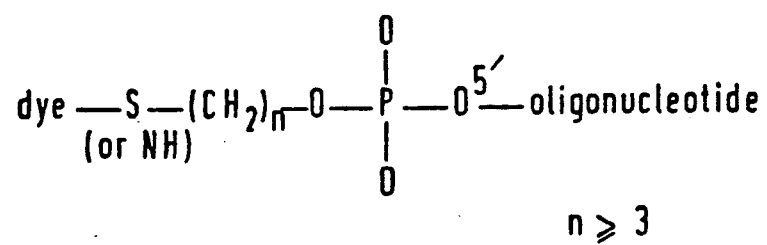

EXAMPLE 1 a) Fluorescence labelling of the primer

5'-(S-triphenylmethyl)-3-mercaptopropylphospho)d[GTAAAA-CGACGGCCAGT] was synthesized and purified as described by Ansorge et al. in J. Biochem. Biophys. Met. 13 (1986), 315–322. 500 nmol silver nitrate was added to 100 nmol of this compound in 0.1 mol/l triethylammonium acetate solution (1 ml, pH 7) and left to stand for 1 hour in an Eppendorf tube. Dithiotreitol (700 nmol) in 100 µl water was added to this and the contents of the tube were mixed and left to stand for 30 minutes. The insoluble silver salt was removed by centrifugation. The supernatant was transferred into a new Eppendorf tube and 1 mol/l aqueous sodium bicarbonate solution was added in order to yield a pH value of 8.5. A solution of 3 mg (6 µmol) 5-iodoacetamidofluorescein (obtained from Molecular Probes, Inc., Eugene, Oreg., USA) in N,N-dimethylformamide (300 µl) was added to this and carefully mixed; then it was kept in the dark for 6 hours. Afterwards 10 µl 2-mercaptoethanol was added in order to remove excess iodoacetamide and then the solution was dialyzed in the dark against water (3×2 l). The solution was concentrated in a vacuum and the primer labelled with dye was purified by ion-exchange HPLC on a Partisil-Sax column using a concentration gradient of potassium dihydrogenphosphate, pH 6.3 in the form of amide/water (6:4 v/v) as eluting agent. This process removes a large part of the strongly associated but not covalently bound dye. The product was desalted by dialysis and further purified by reverse-phase HPLC on a C8-Aquapor RP 300 column using 0.1 mol/l triethylammoniumacetate pH 7/acetonitrile as eluting agent. The completely purified fluorescein-labelled primer was further desalted by dialysis and kept in the dark at −20° C. The yield of dye-labelled primer was 15% based on the S-trityl-material. In the same way a primer labelled with rosin was obtained with a yield of 27%.

b) Sequencing reaction

At first in two preparations 1 µl primer solution, and about 1 to 2 µg single-stranded M13mp18DNA and sequencing buffer were added together to a centrifuge tube to give a total volume of 10 µl to 2 µg M13mp18DNA in a volume of 7 µl was used as a control. The tubes were heated for 2 min to 65° C. then cooled down to room temperature over a period of 30 min. During the cooling the primer hybridizes to its homologous position of the M1—mp18DNA. The hybridization is completed when the temperature has fallen to below 35° C. The following solutions were prepared for the actual sequencing:

| Solution T,C: | 25 µl 0.5 mmol/l dTTP, |
| --- | --- |
| | 25 µl 0.5 mmol/l dCTP, |
| | 500 µl 0.5 mmol/l dGTP and |
| | 500 µl 0.5 mmol/l dATP, |
| | 5 µl 10.0 mmol/l ddTTP, |
| | 1 µl 10.0 mmol/l ddCTP and |
| | 500 µl TE-buffer |
| Solution G,A: | 25 µl 0.5 mmol/l dGTP, |
| | 25 µl 0.5 mmol/l dATP, and |
| | 500 µl each of 0.5 mmol/l dTTP and dCTP, |
| | 5 µl 10 mmol/l ddACT and |
| | 1 µl 10 mmol/l ddGTP together with |
| | 500 µl TE-buffer. |

Figure 2:
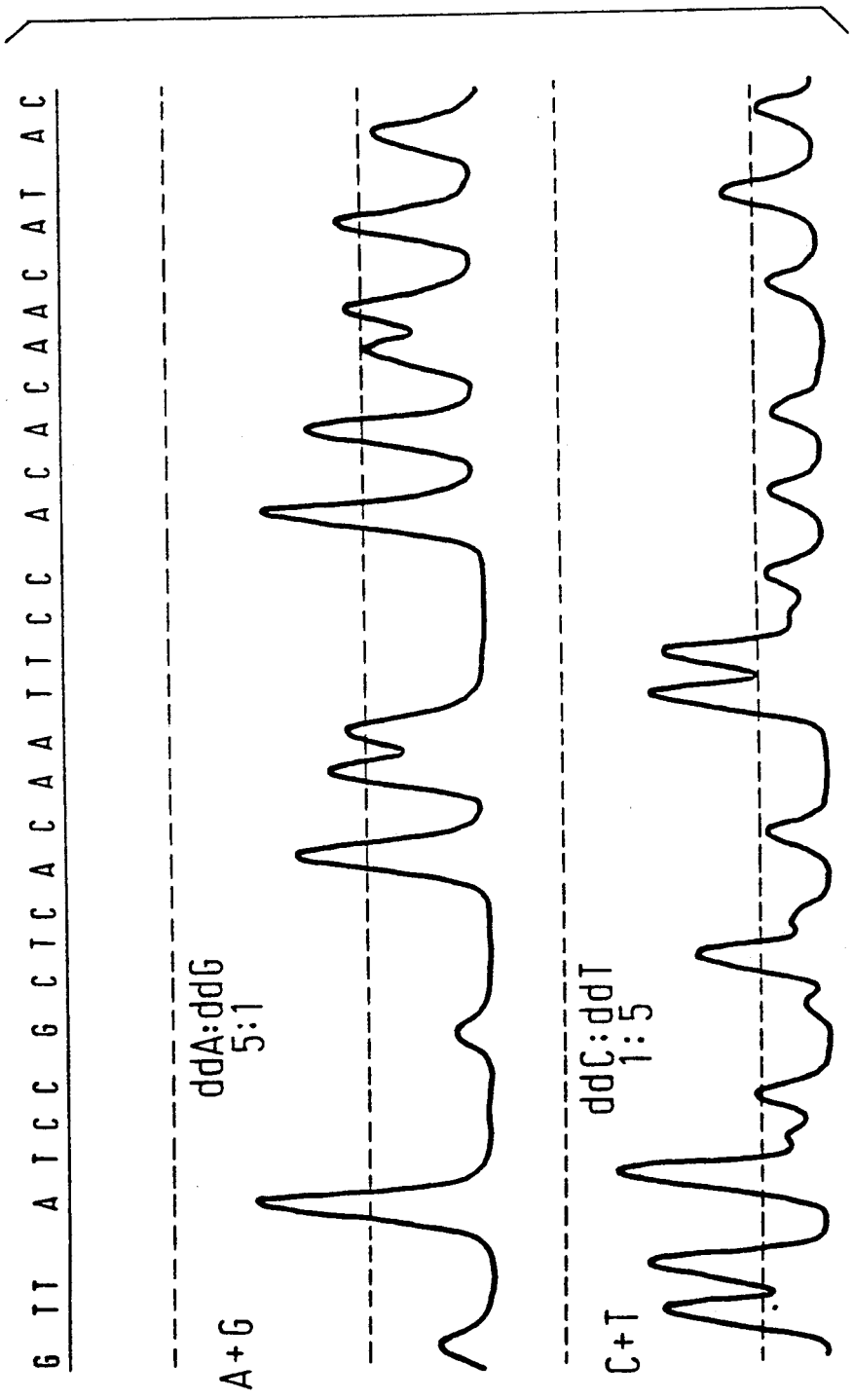
FIG. 2 shows a graph of the peaks of the labelling signal in a sequencing reaction according to the present invention.

Either 2 µl of solution T,C or 2 µl of solution G,A was added to the two samples hybridized with the labelled primer. Afterwards they were incubated for 20 min at room temperature, then 2 µl formamide was added and they were heated for 2 min to 95° C., cooled on ice and loaded on a polyacrylamide gel. FIG. 2 shows a graph of the intensities of the fluorescein, measured in a computer, when the fluoroscein had been excited by a laser for the region of the DNA sequence shown above. For comparison FIG. 3 shows part of the M13mp18DNA in which the sequenced region shown in FIG. 2 is underlined. In the upper curve of FIG. 2 the peaks are shown for fragments which result on addition of ddATP and ddGTP in a ratio of 5:1 in one preparation; in the lower graph the peaks are shown for fragments which result on addition of ddTTP and ddCTP in a ratio of 5:1 in one preparation.

I claim:

1. Method for sequencing a nucleic acid comprising:
   (a) combining
      (i) an oligonucleotide primer,
      (ii) a nucleic acid to be sequenced,
      (iii) four deoxyribonucleoside triphosphates,
      (iv) a polymerase, and
      (v) at least three dideoxyribonucleoside triphosphates in different amounts, under conditions favoring extension of said oligonucleotide primer to form nucleic acid fragments complementary to the nucleic acid to be sequenced;
   (b) labelling the nucleic acid fragments formed;
   (c) separating the nucleic acid fragments by gel electrophoresis; and
   (d) determining nucleic acid sequence by determination of position of incorporated dideoxynucleoside triphosphates in said labelled nucleic acid fragments, wherein said dideoxynucleoside triphosphates are differentiated from each other by intensity of the label in the nucleic acid sequence.

2. Method of claim 1, wherein said three dideoxynucleoside triphosphates are combined with (i), (ii), (iii) and (iv) in two preparations, a first preparation containing different amounts of two dideoxynucleotide triphosphates and a second preparation containing a third dideoxynucleotide triphosphate.

3. Method of claim 1, comprising combining four different dideoxynucleoside triphosphates in different amounts with (i), (ii), (iii) and (iv).

4. Method of claim 3, wherein different amounts of said four dideoxynucleotide triphosphates are combined with (i), (ii), (iii) and (iv) in one preparation.

5. Method of claim 3, wherein different amounts of two different dideoxynucleotides are combined with (i), (ii), (iii) and (iv) in a first preparation and different amounts of a third and a fourth dideoxynucleotide triphosphate are combined with (i), (ii), (iii) and (iv) in a second preparation.

6. Method of claim 2, wherein the two said dideoxyribonucleoside triphosphates present in said first preparation are present in a ratio of about 2:1.

7. Method of claim 3, wherein said four dideoxynucleotide triphosphates are used in a ratio of at least 4:3:2:1.

8. Method of claim 1, wherein said nucleic acid fragments are labelled with a fluorescent dye.

9. Method of claim 8, comprising labelling said nucleic acid fragments by coupling said fluorescent dye to said oligonucleotide primer.

10. Method of claim 9, wherein said fluorescent dye is bound, via a linker, to a 5'-phosphate group of said oligonucleotide primer.

11. Method of claim 8, wherein said fluorescent dye is bound, via a linker to at least one deoxynucleoside triphosphate or at least one dideoxynucleoside triphosphate.

12. Method of claim 11, wherein said fluorescent dye is bound via a linker to one deoxynucleoside triphosphate.

13. Method of claim 11, wherein said fluroescent dye is bound, via a linker, to a C5 position of a pyrimidine.

14. Method of claim 11, wherein said fluorescent dye is bound, via a linker, to a N7, C7 or C8 position of a purine.

15. Method of claim 10 or 11, wherein said linker is a straight chain or branched amino hydrocarbon or a straight chain or branched mercapto hydrocarbon, wherein said hydrocarbon contains an unbranched chain having 3 or more carbon atoms.

16. Method of claim 15, wherein said linker is an aminoalkyl, aminoalkenyl or aminoalkynyl group.

17. Method of claim 1, comprising sequencing a single stranded nucleic acid.

18. Method of claim 1, comprising sequencing a double stranded nucleic acid.

19. Method of claim 8, wherein said fluorescent dye is fluorscein, a fluorescent fluorescin analogue, or rhodamine.

20. Method of claim 2 or 5, wherein said two dideoxynucleoside triphosphates are used in a ratio of X:1, wherein X is a whole number from 5 to 7.

21. Method of claim 3 or 4, wherein said four different dideoxynucleotide triphosphates are used in a ratio of 16:8:4:1.

22. Method of claim 1, wherein said polymerase is Klenow fragment of DNA polymerase I, T7 DNA polymerase, modified T7 DNA polymerase, Taq polymerase or reverse transcriptase.

23. Method of claim 1, wherein said polymerase is T7 DNA polymerase.

24. Method of claim 1, further comprising subjecting said nucleic acid sequence to be determined to polymerase chain reaction prior to determining its sequence to increase the amount of said nucleic acid sequence, separating double stranded nucleic acids thus produced, and using one of the double strands to determine said nucleic acid sequence.

25. Method of claim 8, further comprising exciting said fluorescent dye with a laser in step (d).

* * * * *